United States Patent

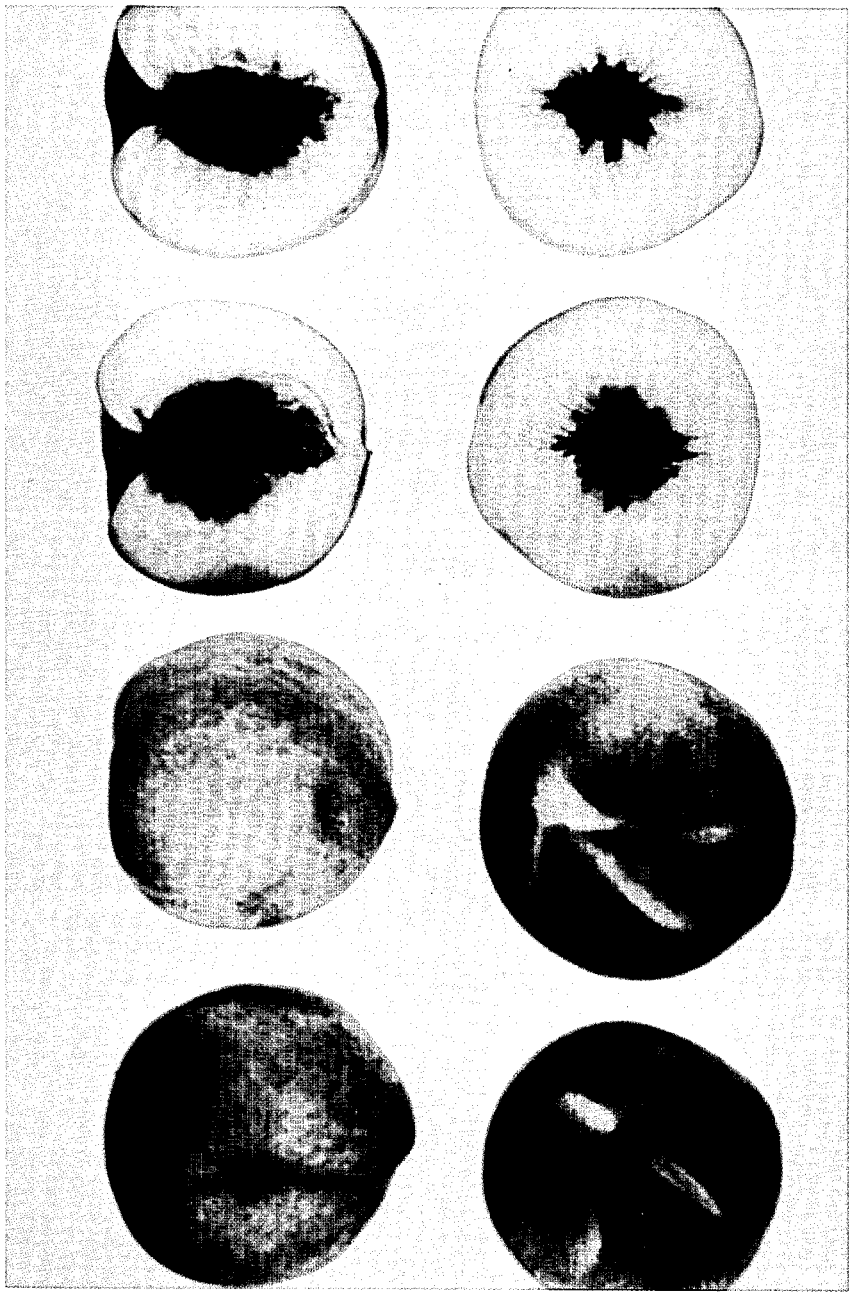

Plant Pat. 3,977

Patented Nov. 16, 1976

3,977

PEACH TREE

Claron O. Hesse, Kingsburg, Calif., assignor to The Regents of the University of California, Berkeley, Calif.

Filed Oct. 20, 1975, Ser. No. 624,150

Int. Cl.[2] A01H 5/03

U.S. Cl. Plt.—43 1 Claim

This invention relates to a new and distinct variety of peach tree which resulted from a complex cross, the pedigree of which is set forth below:

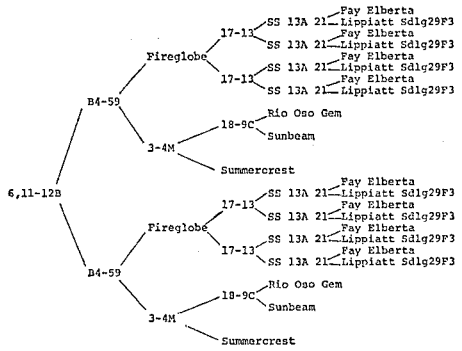

The last step self-pollination of B4-59 was made in 1962.

The invention of Selection 6,11-12B was discovered in 1967 and subsequently asexually multiplied at the Kearney Horticultural Field Station, Fresno County, Calif. in 1968. Thereafter the new variety was placed in several authorized grower-cooperative trial plots and tested. These tests indicated the merit of this new peach tree and resulted in its selection as a promising variety.

FIG. 1 of the accompanying drawing illustrates peaches of the new variety which are typical in size, shape and color, some of which are shown in half sections, pitted and unpitted, and in which some of the variations in the size and shape of the fruit, its pit, and the color of the skin and flesh of this variety are indicated.

A distinguishing characteristic of this new variety of tree resides in its fruit which has a relatively late maturity near the end of August and just before Fairtime and Summerset.

The fruit is further characterized by its development of a high red blush over most of the surface of the fruit prior to shipping maturity combined with a firm, clear, amber-yellow flesh without red flecking or streaking until well past full ripeness on the tree. The fruit hangs well and is firm enough to be picked for shipment when tree ripe, at which time it has a full red blush and is suitable for freezing. The eating quality is very good in that the fruit is rich, sweet and mild with low, but not lacking in acidity. Its perfume is only slightly aromatic.

The varietal characteristics of this new peach tree described below in detail were observed upon its discovery and subsequently through its test period. The color terminology as used herein is in accordance with Ridgway, Color Standards and Color Nomenclature (1912 edition).

Tree:

*Size.*—Medium; vigor medium; upright-spreading with shape and density determined by pruning.

*Current seasons shoots.*—Applegreen, Plate XVII, tinged light red where exposed.

*Trunk.*—Medium stocky, medium rough; brown (Carob Brown, Plate XIV).

*Branches.*—Reddish brown to brown (Carob Brown, Plate XIV to Sudan Brown, Plate III); bark rough, peeling off in recurved platelets which adhere tightly. On younger branches, growth cracks striated showing light brown (Cinnamon-Bluff, Plate XXIX) beneath.

*Lenticels.*—Moderately numerous, medium size; relatively inconspicuous with low, raised lips.

*Flower buds.*—Pump, pubescent.

Leaves: From midshoot leaves of 18" to 22" length shoots.

*Size.*—Average for the species; 16.5±1.60 cm. long x 4.5±0.71 cm. wide. Petiole length 1.1±0.17 cm.

*Shape.*—Ovate-lanceolate to lanceolate; base acuminate; apex long, acute-acuminate.

*Blade.*—Thin; dark green (Elm Green, Plate XVII), lighter beneath. Flat to moderately folded; often more or less twisted. Margin crenate, straight or but slightly wavy. Midrib lightly puberulent laterally near the blade on the under side.

*Petiole.*—Moderately short, stout, channeled on the ventral side. With 2 to 4 glands, 2 of the glands often on the base of the blade.

*Glands.*—Reniform, but weakly so; some appearing to be glabrous, especially if borne on a stalk.

Flowers: 1–2 per node.

*Pedicel.*—Short; 2–3 mm; greenish (Scheele's Green, Plate VI) or slightly tinged red depending upon exposure. Glabrous.

*Corolla.*—Rather short, wide, cup-shaped. Slightly furrowed or grooved basally becoming rugose apically. Reddish throughout dorsally; green ventrally becoming more or less diffused with red (Bordeaux, Plate XII) with age. Nectaries, bright orange (Orange, Plate III) at anthesis becoming a darker, deeper orange with age, more or less furrowed or grooved longitudinally; upper margin wavy, terminating near stamen insertion.

*Calyx lobes.*—Very broad ovate; not widely separated basally, pubescent dorsally marginally, glabrous ventrally. Margin usually entire but occasionally with a slight notch at apex. Often with a small, mucronate gland near apex.

*Petals.*—Large, broad ovate to nearly round, 22.2±1.48 mm. long x 18.6±1.67 mm. wide, slightly cupped; claw short, medium stout; showy. Color light pink (Rose Pink, Plate XII) throughout at anthesis becoming rosaceous basally with age (Pansy Purple, Plate XII). Margin nearly entire; slightly eroded; more or less wavy but not markedly so. Petals often slightly cupped; occasionally nearly flat. Showy phenotype; flowers quite large. Up to 45 mm. across.

*Stamens.*—Slightly short; seldom more than 15 to 16 mm. long. Filaments slender; white at first anthesis but quickly becoming slightly rosy (Amaranth Purple, Plate XII) and rosaceous (Pansy Purple, Plate XII) throughout but deeper basally with age. About 45 in number. Anthers: Medium size and plumpness; rather red (Nopal Red, Plate I) throughout dorsally, buff ventrally (Light Orange-Yellow, Plate III), blushed more or less red. Pollen abundant, yellow (Lemon Chrome, Plate IV), fertile.

*Pistil.*—Long; 16–18 mm. Base obovate, smallish; very pubescent to nearly tomentose; style moderately thin; pubescent basally becoming glabrous throughout upper ¾ or more. Stigma small, capitate. Color greenish (Scheele's Green, Plate VI) or tinged reddish if exposed to direct light.

Fruit:

*Ripe.*—September 1 (full tree ripe).

*Crop.*—Very heavy following extremely heavy set.

*Shape.*—Length 74.4±3.08 mm. x cheek diameter 78.2±2.17 mm. x suture diameter 77.9±2.82 mm.; weight per fruit 246±22.08 gms. Globose to broad ovate; quite regular, uniform, smooth; the base at right angles to or only slightly sloped toward the ventral edge; the apex broad rounded to rounded; the ventral side usually somewhat longer than the dorsal edge. Ventral suture aspect: Broad ovate; nearly or quite symmetrical. Axial aspect: Round or nearly so, very slightly and broadly angular; the ventral half somewhat larger.

*Base.*—Broad flat. At right angles to the fruit axis, or sloping slightly toward the ventral edge. Nearly smooth and regular, or slightly higher laterally. Cavity broad oval to round, medium deep, somewhat narrow to rather broad conic; smooth and regular. Often broadly and obscurely depressed dorsally; usually very lightly creased at the ventral suture within the cavity only. Shoulders: Smoothly and more or less broadly rounded; usually somewhat higher laterally; seldom very lightly creased at the ventral suture.

*Suture.*—A line basally to beyond medianly; often becoming a slightly depressed, very shallow, narrow groove apically. Usually with a low, rounded lip on one side only, the lip more pronounced apically.

*Apex.*—Rounded or occasionally nearly flat. The stylar scar a small dot, often on a low, fleshy tip, not pronounced. Slightly depressed dorsal to the stylar tip.

*Color.*—Ground: amber-yellow (golden) (Apricot Yellow, Plate IV). Blush: Medium to dark red (Coral Red, Plate XIII to Bordeaux, Plate XII). Washed over exposed portions of surface; semi-washed on protected areas. With mottling and rather broad streaking of darker red beneath. Obscurely so on darker areas. More finely streaked along the ventral suture and at the base.

*Pubescence.*—Somewhat sparse, short.

*Fresh color.*—Rich deep yellow to golden (amber) yellow (Primuline Yellow, Plate XVI) with increasing maturity; becoming lightly flecked with red, especially along the ventral suture with full, soft ripeness.

*Cavity color.*—Bright medium red (Nopal Red, Plate I); the red radiating into the flesh to about ⅓ especially with full ripeness.

*Adhesion.*—Full freestone with little or no air space.

*Flesh.*—Very firm until overripe; firm-melting when full ripe. Texture meaty, medium fine.

*Flavor.*—Rich, only slightly aromatic, sweet, mild; acid low but not lacking. Very good.

*Stone.*—Medium size; nearly elliptical to very slightly obovate; mostly quite symmetrical in lateral view; medium or more plump, with one side often slightly more plump than the other. The base broadly but shortly necked; the scar medium or larger, narrow elliptic. The ventral suture narrow, more or less eroded; the wings close, usually somewhat lower, converging apically, more or less rounded; the lateral channels moderately deep, rounded; the whole low and rounded, or protruding but little. The dorsal suture raised, rather narrow, with a rather deep, narrow channel from base to the apex; the sides more or less eroded, variable. The apex usually a more or less blunted acuminate tip, almost continuous with the dorsal edge, but sharply recurved to the ventral suture. More or less deeply pitted and grooved laterally, the grooving generally apical. The ridges rounded to eroded, not sharp. Color, dark brown (Bay, Plate II), stained red (Carmine, Plate I) only at the base.

*Seed.*—Large, ovate to elliptic; testas medium brown (Cinnamon-Rufous, Plate XIV). Moderately plump.

I claim:

1. The new and distinct variety of peach tree herein described and illustrated, and identified by the characteristics enumerated above.

No references cited.

ROBERT E. BAGWILL, Primary Examiner